US012673207B1

(12) United States Patent
Giuffrida

(10) Patent No.: US 12,673,207 B1
(45) Date of Patent: *Jul. 7, 2026

(54) MOVEMENT DISORDER RECOVERY SYSTEM AND METHOD

(71) Applicant: Great Lakes NeuroTechnologies Inc., Cleveland, OH (US)

(72) Inventor: Joseph Giuffrida, Hinckley, OH (US)

(73) Assignee: Great Lakes NeuroTechnologies Inc., Cleveland, OH (US)

( * ) Notice: Subject to any disclaimer, the term of this patent is extended or adjusted under 35 U.S.C. 154(b) by 606 days.

This patent is subject to a terminal disclaimer.

(21) Appl. No.: 17/519,710

(22) Filed: Nov. 5, 2021

Related U.S. Application Data

(63) Continuation of application No. 16/008,453, filed on Jun. 14, 2018, now abandoned, which is a continuation of application No. 11/432,583, filed on May 11, 2006, now Pat. No. 10,022,545.

(51) Int. Cl.
*A61N 1/36* (2006.01)
(52) U.S. Cl.
CPC ..... *A61N 1/36067* (2013.01); *A61N 1/36003* (2013.01)

(58) Field of Classification Search
CPC ............ A61N 1/36003; A61N 1/36067; A61N 1/36128; A61N 1/36132; A61N 1/36135; A61N 1/36139; A61N 1/37247
See application file for complete search history.

(56) References Cited

U.S. PATENT DOCUMENTS

2007/0179534 A1* 8/2007 Firlik ................ A61M 5/14276
604/503

* cited by examiner

*Primary Examiner* — Allen Porter
(74) *Attorney, Agent, or Firm* — Brian Kolkowski

(57) ABSTRACT

The present invention relates to a movement recovery system, and a method of improving the functional motor recovery of a subject with a movement disorder. The present invention provides for a system and method, which in some embodiments can accurately quantify therapy parameters including compliance, task time spent, muscle coordination and functional improvement by utilizing kinetic, gyroscopic or other movement related information, and/or electromyography (EMG) data. In other embodiments, the system and method provide for functional electrical stimulation (FES) to help control the exercise therapy. The present invention further includes the methods of controlling or utilizing the movement related information, EMG and/or FES to detect, monitor, and control the exercise therapy.

20 Claims, 8 Drawing Sheets

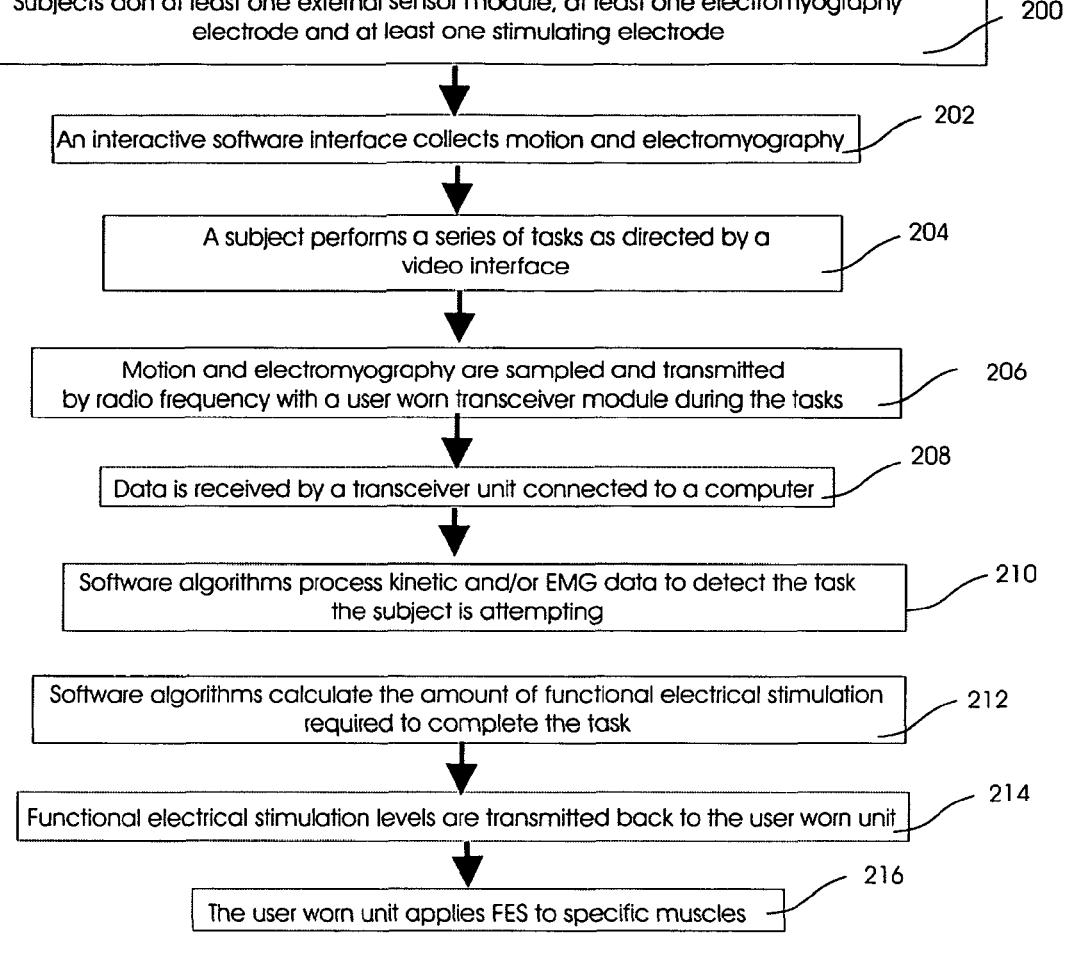

Subjects don at least one external sensor module, at least one electromyography electrode and at least one stimulating electrode — 200

An interactive software interface collects motion and electromyography — 202

A subject performs a series of tasks as directed by a video interface — 204

Motion and electromyography are sampled and transmitted by radio frequency with a user worn transceiver module during the tasks — 206

Data is received by a transceiver unit connected to a computer — 208

Software algorithms process kinetic and/or EMG data to detect the task the subject is attempting — 210

Software algorithms calculate the amount of functional electrical stimulation required to complete the task — 212

Functional electrical stimulation levels are transmitted back to the user worn unit — 214

The user worn unit applies FES to specific muscles — 216

Figure 6

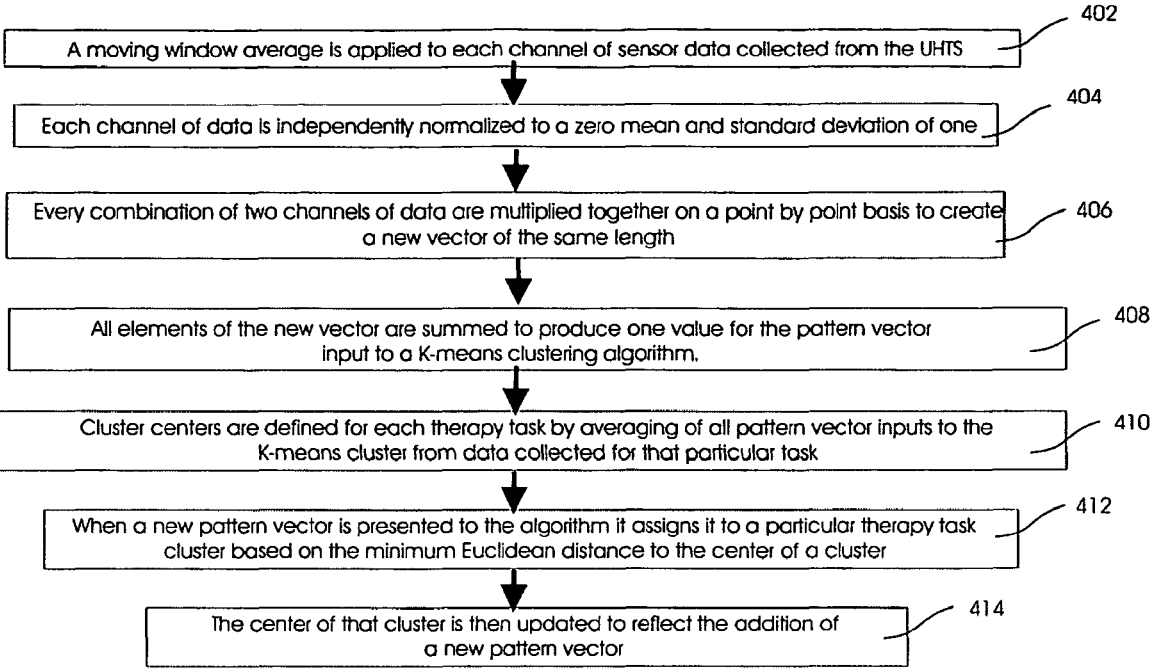

402 A moving window average is applied to each channel of sensor data collected from the UHTS 404 Each channel of data is independently normalized to a zero mean and standard deviation of one 406 Every combination of two channels of data are multiplied together on a point by point basis to create a new vector of the same length 408 All elements of the new vector are summed to produce one value for the pattern vector input to a K-means clustering algorithm.

410 Cluster centers are defined for each therapy task by averaging of all pattern vector inputs to the K-means cluster from data collected for that particular task 412 When a new pattern vector is presented to the algorithm it assigns it to a particular therapy task cluster based on the minimum Euclidean distance to the center of a cluster 414 The center of that cluster is then updated to reflect the addition of a new pattern vector

Figure 8

MOVEMENT DISORDER RECOVERY SYSTEM AND METHOD

CROSS-REFERENCE TO RELATED APPLICATIONS

This application is a continuation of U.S. patent application Ser. No. 16/008,453, which was filed on Jun. 14, 2018 and which is a continuation of U.S. patent application Ser. No. 11/432,583, which was filed on May 11, 2006 and issued as U.S. Pat. No. 10,022,545 on Jul. 17, 2018. The above patents and applications are hereby incorporated by reference in their entirety.

The U.S. Government has a paid-up license in this invention and the right in limited circumstances to require the patent owner to license others on reasonable terms provided for by the terms of grant numbers 2R44NS043816-02, 1R43NS046976-01A1, 1R43NS053032-01, 1R43NS055428-01 from the National Institutes of Health, National Institute of Neurological Disorders and Stroke.

BACKGROUND OF THE INVENTION

1. Field of the Invention

The present invention relates to a movement recovery system, and a method of improving the functional motor recovery of a subject with a movement disorder.

2. Technical Background

Movement disorders resulting from brain or spinal cord injury, or abnormalities affect millions of individuals worldwide. These movement disorders can be the result of stroke, cerebral palsy (CP), Parkinson's disease and the like. Since these injuries or abnormalities can affect most parts of the brain or the spinal cord, the possible results are numerous. Effects can include motor paralysis, sensory disturbances, language difficulties, memory problems, and issues with swallowing or slurred speech. These disorders can also result in loss of motor control of the individual's extremities, including paralysis or weakness, abnormal muscle tone, abnormal posture, abnormal movement synergies and loss of coordination. Many individuals that experience a movement disorder develop a physical disability that affects activities of daily living including eating, dressing and personal hygiene.

There are currently a number of treatments including surgery, physiotherapy, orthoses, and medications, which are used to help counter the effects of movement disorders. Two new treatments have been developed as therapy for movement disorders. These are forced use and functional electrical stimulation.

Occupational and physical therapy contribute to the functional recovery of patients suffering from movement disorders. Research has shown that forced use through repetitive motor activity may provide the basis for motor learning and functional recovery. For example repetitive movement execution or repetitive sensorimotor training may be of great benefit for functional outcomes of motor rehabilitation of the arm and hand. Physical therapy has been found to lead to enhancement of motor function if the individual performs voluntary motor activities with that arm. Methods used by rehabilitation therapists to effectively stimulate functional plasticity and motor recovery include active/passive range of motion, bilateral training, forced use, and constraint induced therapy.

Both simple, isolated, single joint movements and complex movement tasks improve motor recovery. Repetitive training of complex movements has been found to provide significant improvement of motor function in distal and proximal affected upper extremities. Grip strength, another important requirement for daily living, is also significantly improved. The repetitive execution of complex motor movements accelerates and supports functional recovery. Increasing the amount of time spent as well as using behavioral methods to encourage motor learning helps improve function for those individuals suffering from a movement disorder.

Functional electrical stimulation has also been used by therapists to help counter the effects of certain movement disorders. For example, functional electrical stimulation has been found to be advantageous for individuals suffering from CP partially because it is non-invasive and causes minimal side effects. Functional electrical stimulation stimulates the muscles to create a contraction. Some individuals with CP have paralyzed muscles while others with early acquired motor deficits can have difficulty producing selective movements in an affected extremity due to a form of apraxia caused by defective motor planning in early infancy. Therefore, a muscle normally required for a task, but inactive due to CP could potentially be included during therapy using functional electrical stimulation. Additionally, utilizing functional electrical stimulation at the sensory level helps the individual to localize the muscle they are trying to use for a particular task.

While repetitive motor activation of both simple and complex movements may improve the time course and amount of functional recovery and that functional electrical stimulation can improve functional outcomes, unfortunately these treatments can require long stays in a treatment center. What is needed is a system that allows individuals to continue therapy outside a treatment center. What is also needed is a system that allows individuals to be treated without the need for an occupational or physical therapist to be available to apply the treatment. What is still further needed is a system that allows for intensive home treatment of individuals affected with movement disorders.

It is therefore an object of the present invention to provide a system for treating individuals with movement disorders without a therapist applying the treatment. It is still another object of the present invention to provide a system, which provides functional recovery. It is still another object of the present invention to provide system that provides real-time feedback to the individual receiving treatment. It is still further another object of the present invention to provide a system that can assist in providing the individual with cortical reorganization through treatment. It is still further another object of the present invention to provide a portable system which the individual can carry with themselves so they might be treated at home, on vacation or while away from home on business. Finally it is the object of the present invention to provide a system for movement disorder recovery that can be remotely accessed by the clinician or physician.

SUMMARY OF THE INVENTION

The present invention relates to a movement recovery system, and a method of improving the functional motor recovery of a subject with a movement disorder.

The present invention provides for a system and method, which in some instances can accurately quantify therapy parameters including compliance, task time spent, muscle coordination and functional improvement by utilizing kinetic, gyroscopic or other movement related information, and/or electromyography (EMG) data. In other instances, the system and method provide for functional electrical stimulation (FES) to help control the exercise therapy. The present invention further includes the methods of controlling or utilizing the movement related information, EMG and/or FES to detect, monitor, and control the exercise therapy.

The system and method of the present invention may provide a small, lightweight, untethered, easy to don system for home therapy of recovering stroke or cerebral palsy subjects. In other instances, the system or method may allow for greater flexibility by allowing for an intense therapy program at home around a subject's schedule. In even other instances, the system or method may encourage a subject to use a paretic limb with a unique interface and real-time feedback. In still other instances, the system or method may improve therapy for the underprivileged or those living in remote locations where access to such therapy is limited. In still even other instances, the system or method may provide a unique research tool to further quantify the effects of new novel treatments. In still another instance, the system or method allows a physician, clinician or technician to review and modify therapy from an external location such as transmitting reports from a subject's home to a physician's office via the internet so that therapy may be monitored and/or modified on or off line.

In one embodiment, the present invention includes a portable therapy system for rehabilitation of a subject's movement disorder comprising a sensor for measuring a subject's electrical muscle activity having a signal related to the subject's electrical muscle activity and a device for providing a stimulus to the subject to respond to wherein the subject's ability to respond to the stimulus is calculated based in part on the signal for measuring the subject's electrical muscle activity.

In another embodiment, the present invention includes a portable therapy system for rehabilitation of a subject's movement disorder comprising a device for measuring a subject's arm or leg motion comprising at least one motion sensor having a signal for measuring; and a device for providing a stimulus or instructions to the subject to respond to by movement of an arm or a leg being measured wherein the device for measuring a subject's arm or leg motion does not substantially limit the subject's arm or leg motion and the ability to respond to the stimulus or instructions is calculated based in part on the signal for measuring the subject's arm or leg motion.

In still another embodiment, the present invention includes a portable therapy system for rehabilitation of a subject's movement disorder comprising a first sensor for measuring a subject's external body motion having a signal related to the subject's external body motion; a second sensor for measuring a subject's electrical muscle activity having a signal related to the subject's electrical muscle activity; and a device for providing a stimulus or instructions to the subject to respond to wherein the subject's ability to respond to the stimulus or instructions is calculated based in part on the signals of the first and second sensors.

In still another embodiment, the present invention includes a portable therapy system for rehabilitation of a subject's movement disorder comprising a sensor for measuring a subject's electrical muscle activity having a signal related to the subject's electrical muscle activity; a first device providing video and/or audio outputs for providing a task for the subject to perform; and a second device for providing functional electrical stimulation to the subject;

wherein the subject's ability to complete the task is estimated or calculated based in part on the signal for measuring the subject's electrical muscle activity and the second device can be activated in order to assist the subject in completing the task based in part on the estimation or calculation of the subject's ability to complete the task.

In still another embodiment, the present invention includes a portable therapy system for rehabilitation of a subject's movement disorder comprising a first device for measuring a subject's arm or leg motion comprising at least one motion sensor having a signal for measuring; a second device for providing video and/or audio outputs for providing a task for the subject to perform; and a third device for providing functional electrical stimulation to the subject; wherein the subject's ability to complete the task is estimated or calculated based in part on the signal for measuring the motions of the subject's arm and/or leg and the third device can be activated in order to assist the subject in completing the task based in part on the estimation or calculation of the subject's ability to complete the task.

In still another embodiment, the present invention includes a portable therapy system for rehabilitation of a subject's movement disorder comprising a sensor for measuring a subject's electrical muscle activity having a signal related to the subject's electrical muscle activity; a sensor for measuring the subject's body motion having a signal related to the subject's body motion; a first device providing video and/or audio outputs for providing a task for the subject to perform; and a second device for providing functional electrical stimulation to the subject; wherein the subject's ability to complete the task is estimated or calculated based in part both on the signal for measuring the subject's electrical muscle activity and the signal related to the subject's body motion, and the second device can be activated in order to assist the subject in completing the task based in part on the estimation or calculation of the subject's ability to complete the task.

In still another embodiment, the present invention includes a method of rehabilitating a subject having a movement disorder comprising the steps of showing a subject a video; performance of a task involving leg and/or arm motion by the subject in response to the video; measuring the subject's leg and/or arm motion in response to the video with a sensor with an output signal; and calculating with a processor the subject's ability to complete the task based in part on the signal from the sensor.

In still another embodiment, the present invention includes a method of rehabilitating a subject having a movement disorder comprising the steps of showing a subject having legs and/or arms a video; performance of a task involving leg and/or arm motion by the subject in response to the video; measuring the subject's leg and/or arm motion in response to the video with a sensor having an output signal; determining with a processor whether the subject's was able to complete the task based in part on the output signal from the sensor; and if not or if only partially completed, applying functional electrical stimulation to at least one of the subject's legs and/or arms to assist the subject in completing the task.

In still another embodiment, the present invention includes a method of rehabilitating a subject having a movement disorder comprising the steps of placing at least one EMG sensor on a subject's leg and/or arm; showing the subject a video; performance of a task involving a leg and/or arm motion by the subject in response to the video; measuring the subject's leg and/or arm muscle activity in response to the video with the at least one EMG sensor with an output signal placed on the subject's leg and/or arm; and calculating with a processor the subject's ability to complete the task based in part on the output signal from the at least one EMG sensor.

In still another embodiment, the present invention includes a method of rehabilitating a subject having a movement disorder comprising the steps of placing at least one motion sensor on a subject's leg and/or arm; showing the subject a video; performance of a task involving a leg and/or arm motion by the subject in response to the video; measuring the subject's leg and/or arm motion in response to the video with the at least one motion sensor with an output signal placed on the subject's leg and/or arm; and calculating with a processor the subject's ability to complete the task based in part on the output signal from the at least one motion sensor.

In still another embodiment, the present invention includes a method of rehabilitating a subject having a movement disorder comprising the steps of placing at least one motion sensor and at least one EMG sensor on a subject's leg and/or arm; showing the subject a video; performance of a task involving a leg and/or arm motion by the subject in response to the video; measuring the subject's leg and/or arm muscle activity in response to the video with the at least one EMG sensor with a first output signal placed on the subject's leg and/or arm; measuring the subject's leg and/or arm motion in response to the video with the at least one motion sensor with a second output signal placed on the subject's leg and/or arm; and calculating with a processor the subject's ability to complete the task based in part on both on the first output signal from the at least one EMG sensor and the second output signal from the at least one motion sensor.

Additional features and advantages of the invention will be set forth in the detailed description which follows, and in part will be readily apparent to those skilled in the art from that description or recognized by practicing the invention as described herein, including the detailed description which follows, the claims, as well as the appended drawings.

It is to be understood that both the foregoing general description and the following detailed description are merely exemplary of the invention, and are intended to provide an overview or framework for understanding the nature and character of the invention as it is claimed. The accompanying drawings are included to provide a further understanding of the invention, and are incorporated in and constitute a part of this specification. The drawings illustrate various embodiments of the invention; and together with the description serve to explain the principles and operation of the invention.

BRIEF DESCRIPTION OF THE DRAWINGS

FIG. 6. Operational flow diagram showing one embodiment of the movement disorder recovery method with electrical stimulation control.

FIG. 8. Block diagram showing an algorithm for automatically detecting the therapy task that a subject is performing.

DESCRIPTION OF THE PREFERRED EMBODIMENT

Figure 1:
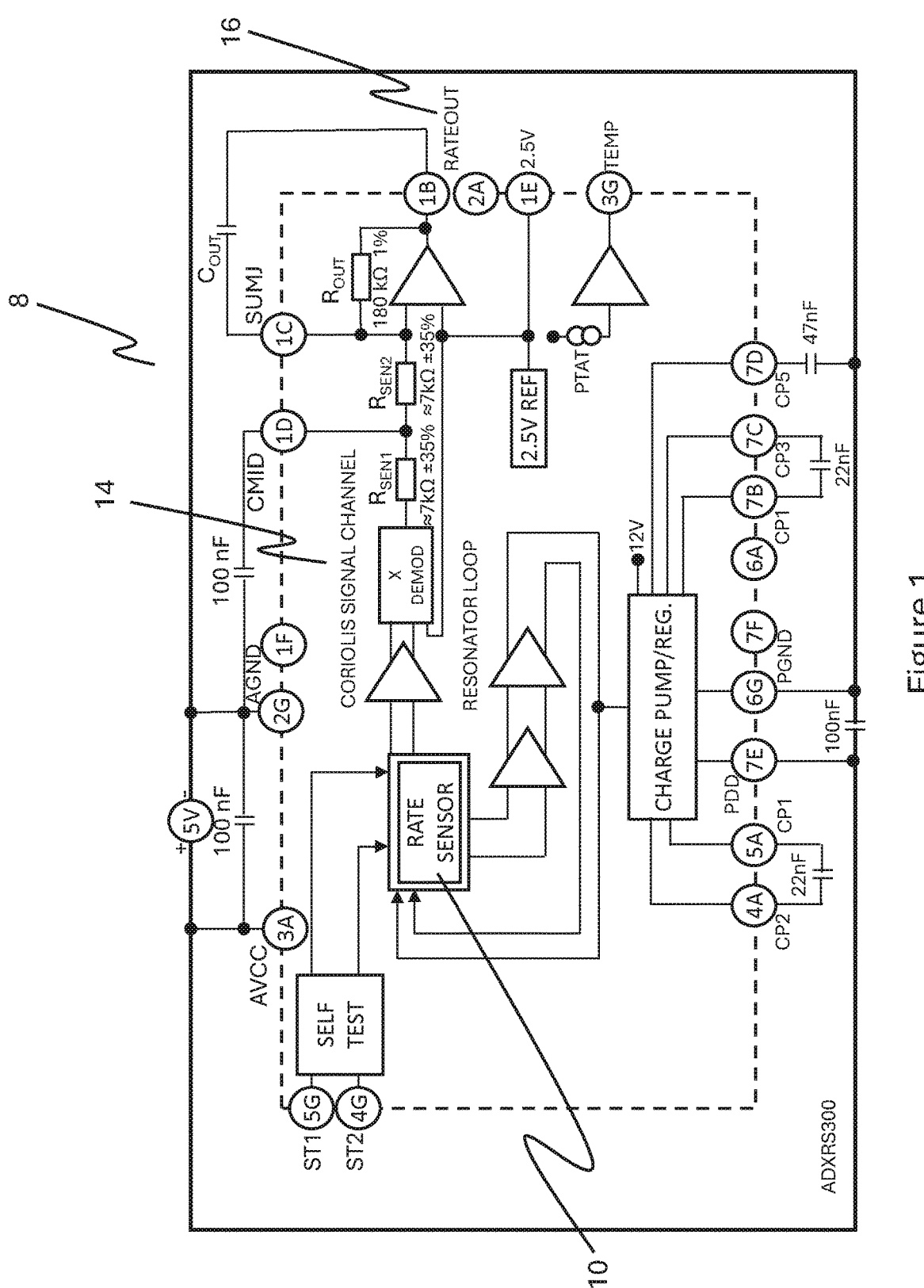
FIG. 1. Electrical schematic of a gyroscope useful in the present invention.

The present invention relates to a movement recovery system, and a method of improving the functional motor recovery of a subject with a movement disorder. The devices, systems and methods of the various embodiments of the present invention are used for continuing and monitoring therapy for various types of movement disorders. Allowing patients to continue therapy in a non-hospital setting such as their home increases time for therapy, and hence the amount of functional improvement. Movement disorders for purposes of this application include but are not limited to those movement disorders stemming from a disease or injury to the nervous system where physical therapy has been or is determined to benefit the subject by either improving the subject's movement or by preventing either further degradation or not as rapid degradation of the subject's condition. Examples of movement disorder that can be treated with the systems and methods of the present invention include but are not limited to stroke and cerebral palsy. The subject on which the devices, system or method is used is a human or other form of animal.

The therapy devices worn by the various subjects or the different systems of the various embodiments of the present invention are preferably portable. By portable it is meant among other things that the device is capable of being transported relatively easily. Relative easy in transport means that the therapy device is easily worn and carried, generally in a carrying case to the point of use or application and then worn by the subject without significantly affecting their range of motion. Furthermore the portable therapy device preferably should be relatively light-weight. By relatively light-weight, preferably the device weighs less than about 3 lbs., more preferably less than about 2 lbs., even more preferably less than about 1 lb., and most preferably less than about 0.5 lbs. By being light-weight and further compact, the therapy device should gain greater acceptance for use by the subject. The entire therapy system including the therapy device, feedback modality, and other components including any processors, computers, video screens and the like preferably weigh less in total than about 15 lbs., more preferably less than about 10 lbs., and most preferably less than about 5 lbs. This system more preferably can fit in a reasonably sized carrying case so the patient or their caregiver can easily transport the system.

The devices of the various embodiments of the present invention can form part of a system for use by a physician, veterinarian, technician or clinician for treatment and further diagnosis of a subject's movement disorder; for pharmaceutical research; or for delivery of pharmaceutical compounds. Other elements of this system may include but are not limited to receivers, routers, communication devices, processors, displays, drug delivery devices and the like, some of which are described further in various embodiments described in more detail below.

Various embodiments of the present invention may include various sensors known to those skilled in the art to sense motion, physiological conditions of the subject and the like. Of these various embodiments of the present invention some may include a sensor for measuring a subject's external body motion. Many types of sensors are known by those skilled in the art for measuring external body motion. These sensors include but are not limited to accelerometers, gyroscopes, magnometers, resistive bend sensors, combinations thereof, and the like. Preferably, a combination using an accelerometer and gyroscope is used. FIG. 1 is an electrical schematic diagram for one embodiment of a gyroscope 8 used as a sensor or in a sensor of the present invention. The sensor element 10 functions on the principle of the Coriolis Effect and a capacitive-based sensing system. Rotation of the sensor 10 causes a shift in response of an oscillating silicon structure resulting in a change in capacitance. An application specific integrated circuit (ASIC) 14, using a standard complimentary metal oxide semiconductor (CMOS) manufacturing process, detects and transforms changes in capacitance into an analog output voltage 16, which is proportional to angular rate. The sensor element design utilizes differential capacitors and symmetry to significantly reduce errors from acceleration and off-axis rotations.

Figure 2:
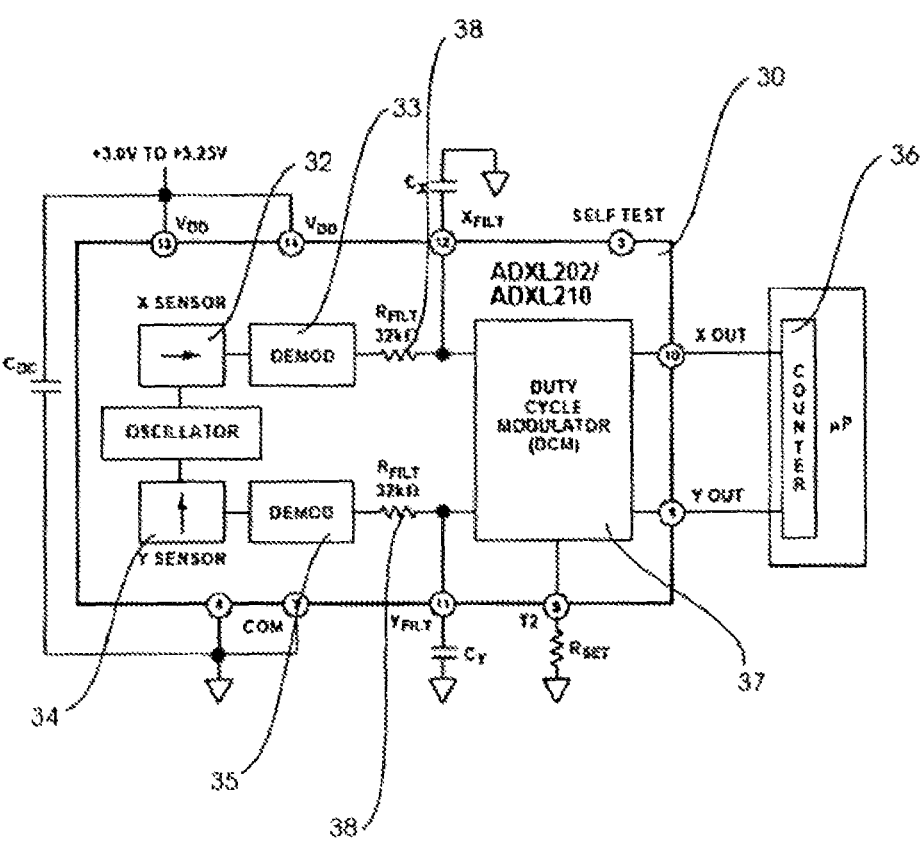
FIG. 2. Electrical schematic of a dual axis accelerometer useful in the present invention.

FIG. 2 (in the current markup they are switched) is an electrical schematic diagram for one embodiment of a dual axis accelerometer of the present invention. The dual axis acceleration measurement system 30 is on a single monolithic IC. They contain a polysilicon surface-micromachined sensor and signal conditioning circuitry to implement an open-loop acceleration measurement architecture. For each axis 32, 34 an output circuit converts the analog signal to a duty cycle modulated (DCM) digital signal that can be decoded with a counter/timer port 36 on a microprocessor. The dual axis accelerometer is capable of measuring both positive and negative accelerations. The sensor 30 is a surface micromachined polysilicon structure built on top of the silicon wafer. Polysilicon springs suspend the structure over the surface of the wafer and provide a resistance against acceleration forces. Deflection of the structure is measured using a differential capacitor that consists of independent fixed plates and central plates attached to the moving mass. The fixed plates are driven by 180-degree out of phase square waves. Acceleration will deflect the beam and unbalance the differential capacitor, resulting in an output square wave whose amplitude is proportional to acceleration. Phase sensitive demodulation techniques are then used to rectify the signal and determine the direction of the acceleration. The output of the demodulator 33, 35 drives a duty cycle modulator (DCM) 37 stage through a 32 kOhm resistor 38. At this point a pin is available on each channel to allow the user to set the signal bandwidth of the device by adding a capacitor. This filtering improves measurement resolution and helps prevent aliasing. After being low-pass filtered, the analog signal is converted to a duty cycle modulated signal by the DCM stage 37. A single resistor sets the period for a complete cycle (T2). A 0 g acceleration produces a nominally 50% duty cycle. The acceleration signal can be determined by measuring the length of the T1 and T2 pulses with a counter/timer or with a polling loop using a low cost microcontroller.

Figure 3:
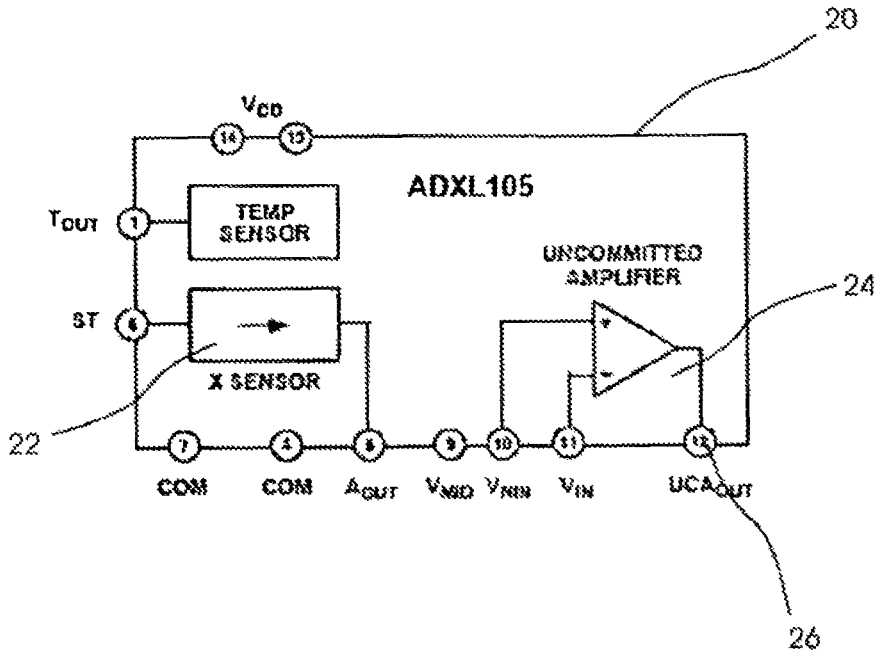
FIG. 3. Electrical schematic of a single axis accelerometer useful in the present invention.

FIG. 3 is an electrical schematic diagram for one embodiment of a single axis accelerometer of the present invention (flipped in the current edit). The accelerometer 20 is fabricated using a surface micro-machining process. The fabrication technique uses standard integrated circuit manufacturing methods enabling all signal processing circuitry to be combined on the same chip with the sensor 22. The surface micro-machined sensor element 22 is made by depositing polysilicon on a sacrificial oxide layer that is then etched away leaving a suspended sensor element. A differential capacitor sensor is composed of fixed plates and moving plates attached to the beam that moves in response to acceleration. Movement of the beam changes the differential capacitance, which is measured by the on chip circuitry. All the circuitry 24 needed to drive the sensor and convert the capacitance change to voltage is incorporated on the chip requiring no external components except for standard power supply decoupling. Both sensitivity and the zero-g value are ratiometric to the supply voltage, so that ratiometeric devices following the accelerometer (such as an analog to digital converter (ADC), etc.) will track the accelerometer if the supply voltage changes. The output voltage (VOUT) 26 is a function of both the acceleration input and the power supply voltage (VS).

Figure 4:
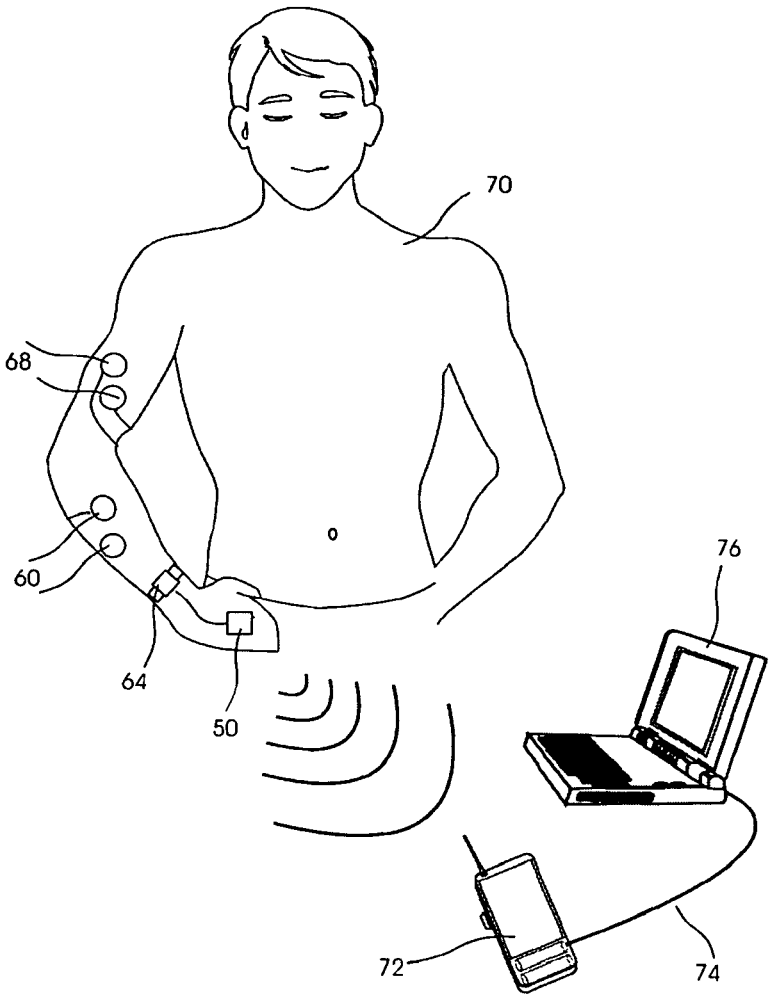
FIG. 4. Schematic showing various system components of the movement disorder recovery device as applied to a subject.

FIG. 4 illustrates one embodiment of the portable rehabilitation therapy system. The computer 76 in this embodiment can provide a stimulus such as video, audio, written or verbal instructions, or some combination thereof. The video can be as simple as a video game which the subject 70 responds to through movement of various parts of the subject's body, which are the focus of the therapy. The external sensor module 50 in this embodiment contains three orthogonal accelerometers (not shown) and three orthogonal gyroscopes (not shown). This input to the external sensor module 50 consists of the kinetic forces applied by the user and measured by the accelerometers and gyroscopes. The output from the board is linear acceleration and angular velocity data in the form of output voltages. These output voltages are input to the transceiver module 64. These voltages undergo signal conditioning and filtering before sampling by an analog to digital converter. This digital data is then transmitted as a packet in RF transmission over a radio link or through a hardwire connection to a computer. Additionally, EMG electrodes 60 worn by the subject may be input to the transceiver module. An amplifier on the transceiver module 64 amplifies the EMG signal(s) before signal conditioning, filtering, and sampling by the analog to digital converter. The EMG data is sent over a hardwire connection to a computer and/or contained in the packet for RF transmission. A microprocessor (not shown) in the transceiver module 64 may control the entire process. Kinetic and EMG data packets may be sent by RF transmission to a nearby computer transceiver 72 which sends the data using a radio connected to a computer 76 or over a hardwire connection. The computer 76 then processes, analyzes, and stores the data. The kinetic sensor board 50 measures accelerations along and angular velocities about each of three orthogonal axes. The signals from the accelerometers and gyroscopes of the kinetic sensor board 50 are preferably input into a processor for signal conditioning and filtering. Preferably, three Analog Devices gyroscopes (ADXRS300) were utilized on the kinetic sensor board with an input range up to 1200 degrees/second. The Analog Devices parts were selected after an analysis of cost, size and power consumption. The ball grid array type of component was selected to minimize size. Additionally, a MEMS technology dual axis accelerometer, from Analog Devices (ADXL210), was employed to record accelerations along the x and y-axes. The sensors provide 80 dB dynamic range, low noise (1 mg/sqrt (Hz)), and low power (<2 mA per axis) in a surface mount package. Other combinations of accelerometers and gyroscopes known to those skilled in the art could also be used. A lightweight plastic housing was then used to house the sensor for measuring the subject's external body motion. The external body motion sensor(s)

can be worn on the subject's finger, hand, wrist, fore arm, upper arm, head, chest, back, legs, feet and/or toes.

Various embodiments of the present invention may include a sensor(s) for measuring the subject's electrical muscle activity through techniques such as electromyography (EMG) or the like. FIG. 4 shows the EMG electrodes 60 and stimulating electrodes 68 which are connected to the transceiver or command module 64. With an EMG sensor, a voltage difference or difference in electrical potential is measured between at least two recording electrodes. The electrodes used can be any type known to those skilled in the art including both indwelling (needle), surface and dry electrodes. Typical EMG electrodes connections may have an impedance in the range of from 5 to 10 K ohms. It is in general desirable to reduce such impedance levels to below 2 K ohms. Therefore a conductive paste or gel may be applied to the electrode to create a connection with an impedance below 2 K ohms. Alternatively, the subject(s) skin may be mechanically abraded, the electrode may be amplified or a dry electrode may be used. Dry physiological recording electrodes of the type described in U.S. patent application Ser. No. 09/949,055 are herein incorporated by reference. Dry electrodes provide the advantage that there is no gel to dry out and no skin to abrade or clean. Additionally if electrodes are used as the sensor(s), preferably at least three electrodes are used—two signal electrodes and one reference electrode.

Preferably, the transceiver module 64 contains one or more electronic components such as the microprocessor 70 for detecting both the signals from the gyroscopes 51 and accelerometers 52, and for detecting the signal from EMG electrode 60. Preferably, the one or more electronic components also filter (and possibly amplify) the detected EMG signals and kinetic motion signals, and more preferably convert these signals, which are in an analog form into a digital signal for transmission to the remote receiving unit or over the hardwire link to the computer. The one or more electronic components are attached to the subject as part of device or system. Further preferably, the one or more electronic components can receive a signal from the remote receiving unit or other remote transmitters or over a hardwire link. The one or more electronic components may include circuitry for but are not limited to for example electrode amplifiers, signal filters, analog to digital converter, radio, a DC power source and combinations thereof. The one or more electronic components may comprise one processing chip, multiple chips, single function components or combinations thereof, which can perform all of the necessary functions of detecting a kinetic or physiological signal from the electrode, uploading data to a computer through a serial link, transmitting a signal corresponding to a kinetic or physiological signal to a receiving unit, delivering functional electrical stimulation, and optionally receiving a signal from a remote transmitter. These one or more electronic components can be assembled on a printed circuit board or by any other means known to those skilled in the art. Preferably, the one or more electronic components can be assembled on a printed circuit board or by other means so its imprint covers an area less than 4 in², more preferably less than 2 in², even more preferably less than 1 in², still even more preferably less than 0.5 in², and most preferably less than 0.25 in². (These sizes need adjustment)

Preferably, the circuitry of the one or more electronic components is appropriately modified so as to function with any suitable miniature DC power source. More preferably, the DC power source is a battery. The most preferred battery of the present invention is lithium powered batteries.

Lithium ion batteries offer high specific energy (the number of given hours for a specific weight), which is preferable. Additionally, these commercially available batteries are readily available and inexpensive. Other types of batteries include but are not limited to primary and secondary batteries. Primary batteries are not rechargeable since the chemical reaction that produces the electricity is not reversible. Primary batteries include lithium primary batteries (e.g., lithium/thionyl chloride, lithium/manganese dioxide, lithium/carbon monofluoride, lithium/copper oxide, lithium/iodine, lithium/silver vanadium oxide and others), alkaline primary batteries, zinc-carbon, zinc chloride, magnesium/manganese dioxide, alkaline-manganese dioxide, mercuric oxide, silver oxide as well as zinc/air and others. Rechargeable (secondary) batteries include nickel-cadmium, nickel-zinc, nickel-metal hydride, rechargeable zinc/alkaline/manganese dioxide, lithium/polymer, lithium-ion and others.

Preferably, the circuitry of the one or more electronic components comprises data acquisition circuitry further including an amplifier that amplifies the EMG, (The gyroscope and accelerometer signals will not need to be amplified.). The data acquisition circuitry is designed with the goal of reducing size, lowering (or filtering) the noise, increasing the DC offset rejection and reducing the system's offset voltages. The data acquisition circuitry may be constrained by the requirements for extremely high input impedance, very low noise and rejection of very large DC offset and common-mode voltages, while measuring a very small signal of interest. Additional constraints arise from the need for a "brick-wall" style input protection against ESD and EMI. The exact parameters of the design, such as input impedance, gain and passband, can be adjusted at the time of manufacture to suit a specific application via a table of component values to achieve a specific full-scale range and passband.

More preferably, a low-noise, lower power instrumentation amplifier is used. The inputs for this circuitry is guarded with preferably, external ESD/EMI protection, and very high-impedance passive filters to reject DC common-mode and normal-mode voltages. Still preferably, the instrumentation amplifier gain can be adjusted from unity to approximately 100 to suit the requirements of a specific application. If additional gain is required, it preferably is provided in a second-order anti-bias filter, whose cutoff frequency can be adjusted to suit a specific application, with due regard to the sampling rate. Still preferably, the reference input of the instrumentation amplifier is tightly controlled by a DC cancellation integrator servo that uses closed-loop control to cancel all DC offsets in the components in the analog signal chain to within a few analog-to digital converter (ADC) counts of perfection, to ensure long term stability of the zero reference.

Preferably, the signals are converted to a digital form. This can be achieved with an electronic component or processing chip through the use of an ADC. More preferably, the ADC restricts resolution to 16-bits due to the ambient noise environment in such chips. Despite this constraint, the ADC remains the preferable method of choice for size-constrained applications such as with the present invention unless a custom data acquisition chip is used because the integration reduces the total chip count and significantly reduces the number of interconnects required on the printed circuit board.

Preferably, the circuitry of the sensor board comprises a digital section. More preferably, the heart of the digital section of the sensor board is the Analog Devices ADVC7020 microcontroller. The Analog Devices ADVC7020 microcontroller contains sufficient data and program memory, as well as peripherals which allow the entire digital section to be neatly bundled into a single carefully programmed processing chip. Still preferably, the onboard counter/timer sections are used to produce the data acquisition timer.

Preferably, the circuitry of the transceiver module comprises a digital section. More preferably, the heart of the digital section of the sensor board is the Atmel ATMEGA128 microcontroller. The Atmel ATMEGA128 microcontroller contains sufficient data and program memory, as well as peripherals which allow the entire digital section to be neatly bundled into a single carefully programmed processing chip. Still preferably, the onboard counter/timer sections are used to produce the data acquisition timer.

Preferably, the circuitry for the one or more electronic components is designed to provide for communication with external quality control test equipment prior to sale, and more preferably with automated final test equipment. In order to supply such capability without impacting the final size of the finished unit, one embodiment is to design a communications interface on a separate PCB using the SPI bus with an external UART and level-conversion circuitry to implement a standard serial interface for connection to a personal computer or some other form of test equipment. The physical connection to such a device requires significant PCB area, so preferably the physical connection is designed to keep the PCB at minimal imprint area. More preferably, the physical connection is designed with a break-off tab with fingers that mate with an edge connector. This allows all required final testing and calibration, including the programming of the processing chip memory, can be carried out through this connector, with test signals being applied to the analog inputs through the normal connections which remain accessible in the final unit. By using an edge fingers on the production unit, and an edge connector in the production testing and calibration adapter, the system can be tested and calibrated without leaving any unnecessary electronic components or too large a PCB imprint area on the final unit.

Preferably, the circuitry for the one or more electronic components comprises nonvolatile, rewriteable memory. Alternatively, if the circuitry for the one or more electronic components doesn't comprise nonvolatile, rewriteable memory then an approach should be used to allow for reprogramming of the final parameters such as radio channelization and data acquisition and scaling. Without nonvolatile, rewriteable memory, the program memory can be programmed only once. Therefore one embodiment of the present invention involves selective programming of a specific area of the program memory without programming the entire memory in one operation. Preferably, this is accomplished by setting aside a specific area of program memory large enough to store several copies of the required parameters. Procedurally, this is accomplished by initially programming the circuitry for the one or more electronic components with default parameters appropriate for the testing and calibration. When the final parameters have been determined, the next area is programmed with these parameters. If the final testing and calibration reveals problems, or some other need arises to change the values, additional variations of the parameters may be programmed. The firmware of various embodiments of the present invention scans for the first blank configuration block and then uses the value from the preceding block as the operational parameters. This arrangement allows for reprogramming of the parameters up to several dozen times, with no size penalty for external EEPROM or other nonvolatile RAM. The circuitry for the one or more electronic components has provisions for in-circuit programming and verification of the program memory, and this is supported by the breakoff test connector. The operational parameters can thus be changed up until the time at which the test connector is broken off just before shipping the final unit. Thus the manufacturability and size of the circuitry for the one or more electronic components is optimized.

Preferably the circuitry of the one or more electronic components includes an RF transmitter. Still preferably includes a Bluetooth™ radio. Another feature of the circuitry of the one or more electronic components preferably is an antenna. The antenna, preferably, is integrated in the rest of the circuitry. The antenna can be configured in a number of ways, for example as a single loop, dipole, dipole with termination impedance, logarithmic-periodic, dielectric, strip conduction or reflector antenna. The antenna is designed to include but not be limited to the best combination of usable range, production efficiency and end-system usability. Preferably, the antenna consists of one or more conductive wires or strips, which are arranged in a pattern to maximize surface area. The large surface area will allow for lower transmission outputs for the data transmission. The large surface area will also be helpful in receiving high frequency energy from an external power source for storage. Optionally, the radio transmissions of the present invention may use frequency-selective antennas for separating the transmission and receiving bands, if a RF transmitter and receiver are used on the electrode patch, and polarization-sensitive antennas in connection with directional transmission. Polarization-sensitive antennas consist of, for example, thin metal strips arranged in parallel on an insulating carrier material. Such a structure is insensitive to or permeable to electromagnetic waves with vertical polarization; waves with parallel polarization are reflected or absorbed depending on the design. It is possible to obtain in this way, for example good cross polarization decoupling in connection with linear polarization. It is further possible to integrate the antenna into the frame of a processing chip or into one or more of the other electronic components, whereby the antenna is preferably realized by means of thin film technology. The antenna can serve to just transfer data or for both transferring data to and for receiving control data received from a remote communication station which can include but is not limited to a wireless relay, a computer or a processor system. Optionally, the antenna can also serve to receive high-frequency energy (for energy supply or supplement). In any scenario, only one antenna is required for transmitting data, receiving data and optionally receiving energy. Optionally, directional couples can be arranged on the transmitter outputs of the remote communication station. The couplers being used to measure the radiated or reflected radio wave transmission output. Any damage to the antenna (or also any faulty adaptation) thus can be registered, because it is expressed by increased reflection values.

In any RF link, errors are an unfortunate and unavoidable problem. Analog systems can often tolerate a certain level of error. Digital systems, however, while being inherently much more resistant to errors, also suffer a much greater impact when errors occur. Thus the present invention when used as a digital system, preferably includes an error control sub architecture. Preferably, the RF link of the present invention is digital. RF links can be one-way or two-way. One-way links are used to just transmit data. Two-way links are used for both sending and receiving data.

Preferably, the RF link utilizes a two-way (bi-directional) data transmission. By using a two-way data transmission the data safety is significantly increased. By transmitting redundant information in the data, the remote communication station is capable of recognizing errors and request a renewed transmission of the data. In the presence of excessive transmission problems such as, for example transmission over excessively great distances, or due to obstacles absorbing the signals, the remote communication station is capable of controlling the data transmission, or to manipulate on its own the data. With control of data transmission it is also possible to control or re-set the parameters of the system, e.g., changing the transmission channel. This would be applicable for example if the signal transmitted is superimposed by other sources of interference then by changing the channel the remote communication station could secure a flawless and interference free transmission. Another example would be if the signal transmitted is too weak, the remote communication station can transmit a command to increase its transmitting power. Still another example would be the remote communication station to change the data format for the transmission, e.g., in order to increase the redundant information in the data flow. Increased redundancy allows transmission errors to be detected and corrected more easily. In this way, safe data transmissions are possible even with the poorest transmission qualities. This technique opens in a simple way the possibility of reducing the transmission power requirements. This also reduces the energy requirements, thereby providing longer battery life. Another advantage of a two-way, bi-directional digital data transmission lies in the possibility of transmitting test codes in order to filter out external interferences such as, for example, refraction or scatter from the transmission current. In this way, it is possible to reconstruct falsely transmitted data.

The remote communication station of various embodiments of the present invention can be any device known to receive RF transmissions used by those skilled in the art to receive transmissions of data. The remote communication station by way of example but not limitation can include a communications device for relaying the transmission, a communications device for re-processing the transmission, a communications device for re-processing the transmission then relaying it to another remote communication station, a computer with wireless capabilities, a PDA with wireless capabilities, a processor, a processor with display capabilities, and combinations of these devices. Optionally, the remote communication station can further transmit data both to another device and/or back. Further optionally, two different remote communication stations can be used, one for receiving transmitted data and another for sending data. For example, with the home therapy system of the present invention, the remote communication system of the present invention can be a wireless router, which establishes a broadband Internet connection and transmits the physiological signal to a remote Internet site for analysis, preferably by the subject's physician. Another example is where the remote communication system is a PDA, computer or cell phone, which receives the physiological data transmission, optionally re-processes the information, and re-transmits the information via cell towers, land phone lines or cable to a remote site for analysis. Another example is where the remote communication system is a computer or processor, which receives the data transmission and displays the data or records it on some recording medium, which can be displayed or transferred for analysis at a later time.

The digitized kinetic or physiological signal is then, preferably, transmitted wirelessly to a remote communication station, see FIG. 4. This remote communication station allows the subject wide movement. Preferably, the remote communication station can pick up and transmit signals from distances of greater than about 5 feet from the subject, more preferably greater than about 10 feet from the subject, even more preferably greater than about 20 feet from the subject, still even more preferably greater than about 50 feet from the subject, still even more preferably greater than about 200 feet from the subject, and most preferably greater than about 500 feet from the subject. The remote communication station is used to re-transmit the signal or reports based in part from the physiological signal from the remote communication station wirelessly or via the internet to another monitor, computer or processor system. This allows the physician or monitoring service to review the subjects physiological signals and if necessary to make a determination, which could include modifying the patients treatment protocols.

Optionally, the system of the present invention includes some form of instruction, which can be in written form on paper or on a computer monitor, or on a video. Preferably, a video is used which instructs the subjects to perform a series of tasks during which their kinetic motion and/or EMG can be measured. Since the system of the present invention is preferably used in the subject's home, a video giving directions and/or describing various tasks to be performed by the subject is included with the system. The video may be accessed or viewed for example but not by way of limitation through use of video tape, DVD, as part of computer software provided, through the internet, or the like. The directions could include but are not limited to instructions on how to don the device, how to turn the device on, and the like. The description of various tasks could include but is not limited to exercises which are typically used by a technician, clinician or physician or therapist to treat a subject with a movement disorder including but not limited to hand grasps, finger tapping exercises, other movements and the like. One embodiment of a video includes the technician, clinician or physician looking into the camera, as they would a patient, and instructing them on device setup, instructing the patients through each of the tasks to be performed, providing verbal encouragement via video after a task, and asking subject's to repeat a task if it was not completed. Preferably, these video clips are edited and converted to a MPEG files using a Pinnacle Studios digital video system that includes a fire-wire card and editing software. For movement disorders such as stroke preferably the technician, clinician or physician instructs the user through multiple tasks that would normally be completed in their in clinic therapy session. More preferably, if the video is linked to the user interface software, the software will automatically detect if a subject has performed the requested task and provide feedback through the video to either repeat the task or continue to the next task. The motions of the user may also be used to control a video game interface and determine if functional electrical stimulation is required to assist with the task.

The present invention includes various methods of measuring a subject's motion and muscle activity and using those parameters to provide feedback and control for therapy. These methods include a number of steps which may include but are not limited to measuring a subject's external body motion; transmitting wirelessly or over a hardwire link a signal based in part on the subject's measured external body motion; receiving the wirelessly transmitted signal or over a hardwire link; and providing feedback or functional electrical stimulation based in part on the signal.

Various embodiments of the present invention include a device for providing functional electrical stimulation (FES) to the subject. FES is advantageous compared to other stroke therapies since it can be non-invasive with minimal side effects. The system may utilize FES with electrodes placed on the surface of the skin or with implanted electrodes. FES electrically stimulates muscles to create a contraction. Some movement disorder patients have paralyzed muscles while others have weak muscles that are over powered by spasticity of an opposing muscle group. Therefore, a muscle normally required for a therapy, but inactive due to a movement disorder can be included during therapy using FES. In addition, using FES at the sensory level helps the subject to localize the muscles used for a particular therapy task. Sensory stimulation in conjunction with physiotherapy may improve motor skills. Providing feedback from the subject's own movements facilitates motor learning and may drive cortical reorganization.

The main components of an FES system of various embodiments of the present invention are the electrodes, the stimulator, and sensors or switches. When FES is being used to move muscles, current pulses in the electrodes cause the weakened or paralyzed muscles to contract. In other applications, currents in the electrodes may produce electrical currents in the tissues without moving any muscles. The stimulator controls the strength and timing of the low-level pulses that flow to the electrodes. The sensors or switches control the starting and stopping of the pulses supplied by the stimulator.

Many modes of a FES device or system can be used in the movement disorder recovery system and methods of the present invention. Two modes which are used by way of example but not limitation include 1) adaptively modulating stimulation during therapy, and 2) increase muscle strength through exercise.

One embodiment of the FES device, unit or system of the present invention is a battery powered device. This device can deliver up to four channels of stimulation using a 3.7V Lithium Polymer rechargeable battery. Each channel can deliver electrical impulses to a different target muscle. This device uses a two-stage stimulator power supply, which multiplies the small voltages from the battery into a voltage large enough for the desired stimulation. Each stage has a charge pump which pulls the charge directly from the batteries. Stage one produces five volts, while stage two produces 60 volts and contains the high voltage section and the main power regulator for the circuit. The 60 volts is produced by the high voltage section, which is comprised of a charge pump and two 2.2 µF capacitors placed in series. Each capacitor can hold up to 35 volts of charge. A bleed-off branch funnels any excess charge from the capacitors back to the charge pump, which acts as a feedback regulator preventing the charge pump from pulling more charge from the batteries. In this way, energy is not wasted. An LED is designed into the second stage to indicate voltage. The main power regulator produces 3.3 volts for the rest of the circuit.

The stimulator is attached to an Atmel Atmega 128L microprocessor running at 8 MHz. This acts as the central control unit for the stimulator. The unit includes two serial ports, an SPI port, and multiple timers and counters. The four output channels are set on the digital to analog converter using the SPI port. The digital to analog converter drives the amplitude of the four channels in the output stage The output stage is where the stimulation pulse is delivered. This phase is used to charge up the capacitors, which are then discharged. This is called the cathodic stimulating phase. The capacitors are recharged during the anodic recharging phase. The digital to analog converter sets the amplitude levels for each of the four channels. The converter has eight bits of resolution, which results in 0.2 mA steps from 0 to 50 mA. This analog output (for each channel) goes through the buffer amplifiers, which in turn control the gate on the output transistor. The speed at which the charge comes off the capacitors depends on the amplitude hitting the gate of the output transistor. This speed determines the amount of the stimulating current. When the capacitors discharge, the control unit turns off the cathodic phase and enables the capacitors to recharge (the anodic phase). During recharging, the control center connects the high voltage section to the output capacitor through a current-limiting FET circuit.

While a wireless device(s) is the preferred for the present system, the portable therapy system may also be a tethered system or a partially tethered partially wireless system.

Figure 5:
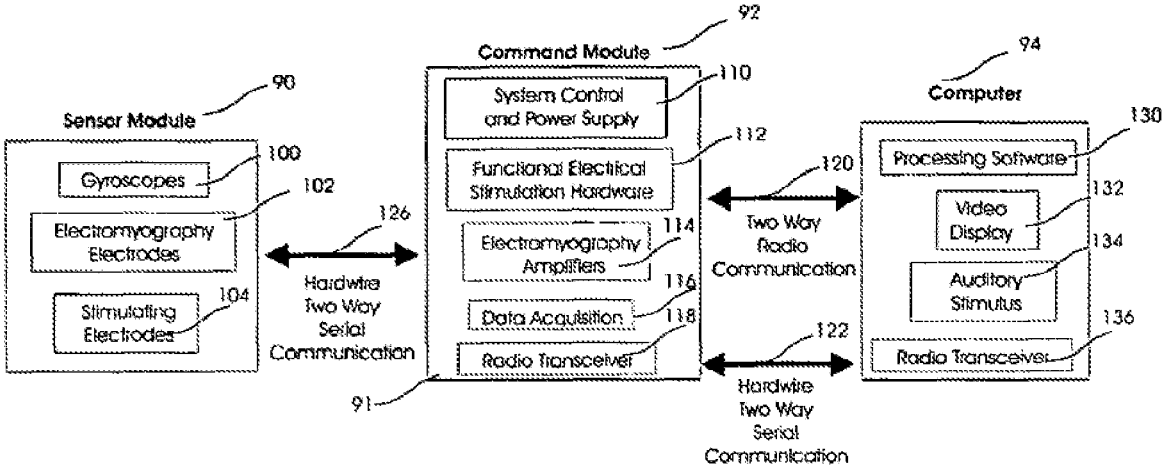
FIG. 5. Block diagram of one embodiment of the movement disorder recovery system.

FIG. 5 is a block diagram showing one embodiment of the movement disorder recovery system of the present invention. The portable therapy rehabilitation system 91 of the present invention preferably comprises three modules or components: a sensor module 90, a command module 92 and a computer or processor 94. The sensor module 90 preferably further comprises at least one gyroscope 100 or other form of motion sensor, an EMG electrode(s) 102, and a stimulating or functional neuromuscular stimulating device 104. The command module 92, to which the sensor module 90 is hardwired 106 enables the signals from the sensors 100, 102 showing the subject's movement to be processed and transmitted to a computer 94. The command module 92 can also be used to either relay or calculate when to apply functional neuromuscular stimulation through the stimulating electrode 104. The command module 92 preferably comprises a system control and power supply 110 for those devices worn by the subject, functional neuromuscular hardware 112 described earlier in the application, EMG amplifiers 114, data acquisition electronics 116 and optionally a radio transceiver 118. Preferably, the command module 92 communicates with a computer or display device 94 via wireless two way radio communication 120 or a tethered, two way serial communication ports on each of the modules 92, 94. If a computer is used preferably, the computer comprises processing software 130, a video display 132, auditory stimulus 134 and a radio transceiver 136 or serial port (not shown).

FIG. 6 is an operational flow diagram showing one embodiment of the movement disorder recovery method of the present invention with electrical stimulation control. In this embodiment, the subject dons at least one external sensor, at least one EMG electrode and at least one stimulating electrode 200. An interactive software interface collections motion and EMG signals 202. The subject is provided a stimulus such as a video requiring the performance of a series of tasks as directed by a video interface 204. Motion and electromyography are sampled from the subject and transmitted to a computer by a radio transceiver module worn by the subject during these tasks 206. Data is received by a transceiver unit connected to or part of the computer 208. Software algorithms in the computer calculate the amount of functional neuromuscular stimulation required to complete the task 210. Functional neuromuscular stimulation levels are transmitted back to the subject worn device 212. The subject worn unit then applies electrical stimulation to specific muscles 214.

Figure 7:
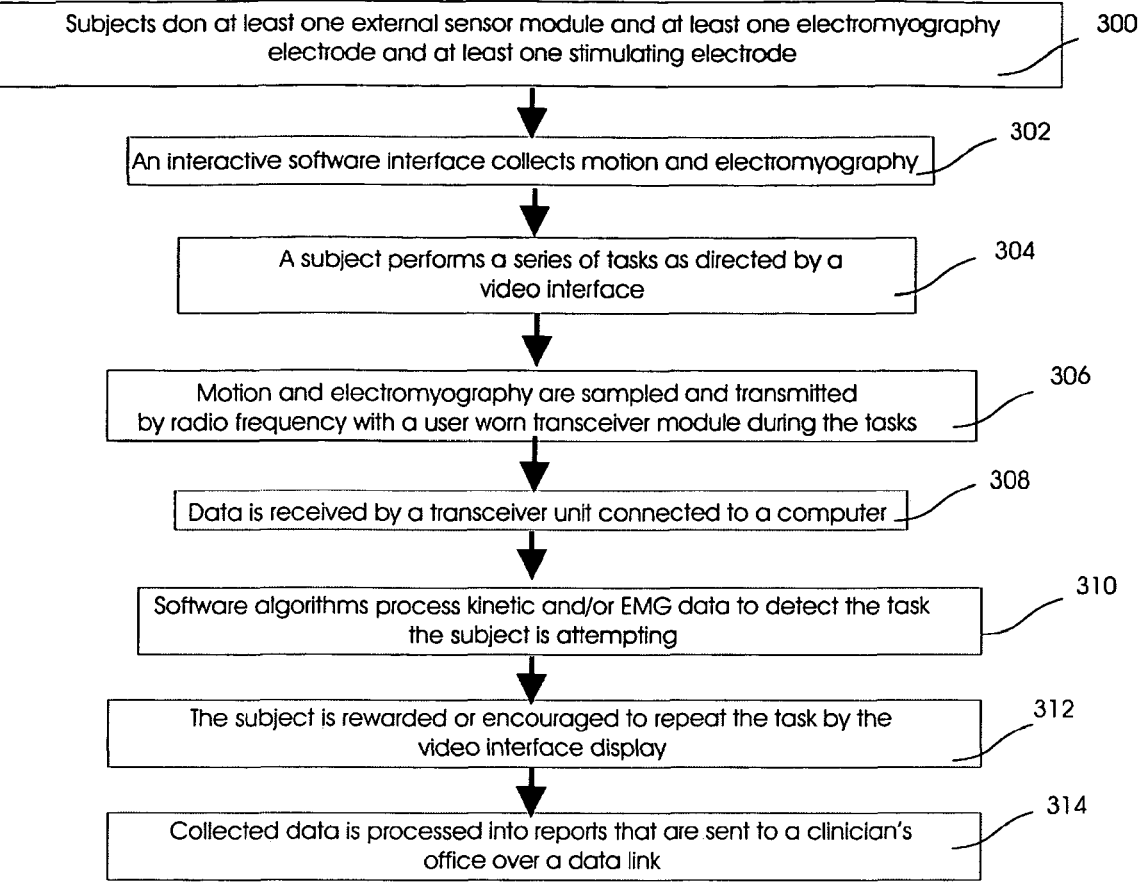
FIG. 7. Operational flow diagram showing one embodiment of the movement disorder recovery method highlighting the patient feedback and system reporting.

FIG. 7 is an operational flow diagram showing another embodiment of the movement disorder recovery method highlighting the patient feedback and system reporting. In this embodiment, the subject dons at least one external sensor, at least one EMG electrode and at least one stimulating electrode 300. An interactive software interface collections motion and EMG signals 302. The subject is provided a stimulus such as a video requiring the performance of a series of tasks as directed by a video interface 304. Motion and electromyography are sampled from the subject and transmitted to a computer by a radio transceiver module worn by the subject during these tasks 306. Data is received by a transceiver unit connected to or part of the computer 308. Software algorithms in the computer calculate the amount of functional neuromuscular stimulation required to complete the task 310. The subject is rewarded or encouraged to repeat the task by the video interface display 312. Collected data is processed into reports that are sent to a clinician's office over a data link 314.

FIG. 8 is a block diagram showing one embodiment of an algorithm for automatically detecting the therapy task a subject is performing. In FIG. 8, the system software integrates algorithms for automated detection of a therapy task (FIG. 8) a person is performing for real-time subject feedback about repetitions and/or task time remaining. The algorithm uses inputs from different combinations of EMG, accelerometers, and/or gyroscopes to automatically classify therapy tasks performed by a subject. One very important difference in stroke subjects, for example, compared to normals is that we not only need to detect when they "are" performing a task, but also when they are "attempting" to perform a task. For further example, someone who cannot yet move their wrist joint may produce repeatable patterns in elbow muscles as they are "attempting" to move their wrist. Different stroke subjects will have different remaining voluntary muscles sets based on their specific injury. Therefore, large variations in coordinated muscle activity may exist between subjects for the same therapy task as well as some variation within a single subject. The algorithm allows generalization of features to produce high accuracy task discrimination.

Each subject may have unique remaining voluntary muscles and coordination patterns. It would not be reasonable to assume that a single, hard coded algorithm could be developed to distinguish tasks among every potential subject. Therefore, instead of a hard coded algorithm, the system includes an algorithm structure that can be quickly trained in a clinician's office during a single office visit while the subject completes therapy tasks as part of their normal visit.

Additionally, it is important to remember that the goal is for these subjects to improve motor control over time. Therefore, as they use the system more and more, coordination patterns of motion and EMG should continue to change, albeit slowly. Therefore, the algorithm structure should adaptively learn over time while the subject's motor function improves. Finally, the algorithm takes advantage of the fact that the therapy exercises are repetitive motions. These repetitive motions should produce specific patterns in a subset of the signals being recorded.

The algorithm utilizes a K-means clustering algorithm. The K-means algorithm provides many advantages including fast training and the ability to continue to add new data over time to adaptively learn improving subject coordination patterns. The K-means algorithm defines a set of cluster centers of n-dimensions where n is the number of quantitative input features used to describe a task trial. Once the cluster centers are defined the n quantitative features of a single trial are compared to each of the cluster centers. The Euclidean distance of all the quantitative features is calculated to each cluster center. The trial is then assigned to the cluster center that has the closest Euclidean distance. That cluster center is then updated to reflect the additional value added to it.

Quantitative input features are extracted for each therapy task completed by a subject. The following quantitative feature inputs are extracted from the system sensors for the K-means algorithm. Each signal was moving window averaged. Next, each channel for each trial was independently normalized to a zero mean and standard deviation of one. In other words, normalization for a particular data channel and trial depended only on that channel and trial. This achieved two goals. First it eliminated the need for a general normalization to maximum and minimum values collected in a calibration routine. Secondly, it did not penalize muscle activity for being of small amplitude. Next, every combination of channels was multiplied together on a point-by-point basis to create a new vector of the same length. That new vector was then summed to create one K-means input. This technique proved valuable as it described if muscles acted agonistically or antagonistically during a therapy task. If muscles act as agonists it produces very large positive numbers. If they act as antagonists, it produces very large negative numbers. Little positive or negative correlation between the muscles produces numbers closer to zero.

Initial cluster centers are defined for each task by calculating the average of the pattern vectors for data collected for each task during system training. New patterns are assigned to particular clusters based on their Euclidean distance from the cluster center. New pattern vectors are assigned to the cluster whose center is the closest Euclidean distance away.

The motion and EMG patterns a subject generates for a particular therapy task will likely change as motor recovery occurs. However, these changes should take place slowly over time. Therefore, the algorithm for task classification needs to adaptively learn the new coordination patterns of a subject. Due to the fact that recovery occurs slowly, the clustering algorithm adaptively updates the cluster centers each time a new pattern is added during system use. In one embodiment of the algorithm represented by FIG. 8, a moving average is applied to each channel of sensor data collected 402, then each channel of data is independently normalized to a zero mean and standard deviation of one 404, then every combination of two channels of data are multiplied together on a point by point basis to create a new vector of the same length 406, this is followed by all the elements of the new vector being summed to produce one value for the pattern vector input to a K-means clustering algorithm 408, next cluster centers are defined for each therapy task by averaging all the pattern vector inputs to the K-means cluster from data collected for that particular task 410, when a new pattern vector is presented to the algorithm it assigns it to a particular therapy task cluster based on the minimum Euclidean distance to the center of the cluster 412, and finally the center of that cluster is updated to reflect the addition of a new pattern vector 414.

It will be apparent to those skilled in the art that various modifications and variations can be made to the present invention without departing from the spirit and scope of the invention. Thus, it is intended that the present invention cover the modifications and variations of this invention provided they come within the scope of the appended claims and their equivalents.

What is claimed:

1. A portable therapy system for rehabilitation of a subject's movement disorder comprising:
   a first sensor for measuring a subject's electrical muscle activity having a signal related to the subject's electrical muscle activity;
   a second sensor for measuring the subject's body motion having a signal related to the subject's body motion;
   a device for providing a stimulus or instructions to the subject, the stimulus or instructions adapted to evoke a response from the subject in the form of electrical muscle activity being measured;
   a therapy device adapted to provide therapy to the subject according to preprogrammed therapy parameters or determined therapy parameters where the determined therapy parameters are based in part on prior measured electrical activity from the subject measured in response to a prior stimulus or instructions; and
   a two-way communication system comprising a remote communication station, the remote communication station configured to be situated more than 200 feet away from the subject, the communication system adapted to:
      1) Allow communication between components local to the subject, including at least the first and second sensors and the device for providing a stimulus or instructions to the subject, and the remote communication station,
      2) Transmit measured data to the remote communication station and receive data related to the measured data and/or to therapy parameters from the remote communication station,
      3) Transmit therapy parameters to the subject's therapy device such that the therapy device provides therapy to the subject according to the adjusted therapy parameters,
   a processor programmed to:
      1) Determine a task or activity the subject is performing based on measured electrical muscle activity, the body motion, and the stimulus or instructions provided to the subject, and
      2) Calculate adjusted therapy parameters based at least in part on the subject's response to the stimulus or instructions and in part on the determined task or activity; and
   wherein the processor is further programmed to calculate the subject's ability to respond to the stimulus based in part on the signals of the first and second sensors.

2. The portable therapy system in claim 1, wherein the therapy device is a device worn by the subject to provide FES to at least one of the subject's muscles to supplement a response of the subject.

3. The portable therapy system in claim 1, wherein the remote communication system is configured to re-transmit the signals of the first and second sensors and/or reports based on said sensor signals wirelessly or via the internet to another monitor, computer, or processor system.

4. The portable therapy system in claim 1, wherein the processor is comprised in the remote communication station, the remote communication station being a cell phone or computer.

5. The portable therapy system in claim 4, wherein the stimulus is a video game.

6. The portable therapy system in claim 1, wherein the system weight is less than 15 lbs.

7. The portable therapy system in claim 3, wherein the two-way communication system is further configured to provide an interface to enable a physician, clinician, or technician to access the signal related to the electrical muscle activity and the signal related to subject's body motion, and the preprogrammed or determined therapy parameters.

8. A portable therapy system for rehabilitation of a subject's movement disorder comprising:
   a device for measuring a subject's arm or leg motion comprising at least one motion sensor having a signal related to the subject's arm or leg motion;
   a device for providing a stimulus or instructions to the subject, the stimulus or instructions adapted to evoke a response from the subject in the form of arm or leg motion being measured;
   a therapy device adapted to provide therapy to the subject according to preprogrammed therapy parameters or determined therapy parameters where the determined therapy parameters are based in part on arm or leg motion of the subject measured in response to a prior stimulus or instructions; and
   a two-way communication system comprising a remote communication station, the remote communication station configured to be situated more than 200 feet away from the subject, the communication system adapted to:
      1) Allow communication between components local to the subject, including at least the sensor and the device for providing a stimulus or instructions to the subject, and the remote communication station,
      2) Transmit measured data to the remote communication station and receive data related to the measured data and/or to therapy parameters from the remote communication station,
      3) Transmit therapy parameters to the subject's therapy device such that the therapy device provides therapy to the subject according to the adjusted therapy parameters,
   a processor programmed to:
      1) Determine a task or activity the subject is performing based on measured electrical muscle activity and the stimulus or instructions provided to the subject, and
      2) Calculate adjusted therapy parameters based at least in part on the subject's response to the stimulus or instructions and in part on the determined task or activity; and
   wherein the device for measuring a subject's arm or leg motion does not substantially limit the subject's arm or leg motion and the processor is further programmed to calculate the subject's ability to respond to the stimulus or instructions based in part on the signal for measuring the subject's arm or leg motion.

9. The portable therapy system in claim 8, wherein the therapy device is a device worn by the subject to provide FES to at least one of the subject's muscles to supplement a response of the subject.

10. The portable therapy system in claim 8, further comprising a second sensor for measuring the subject's electrical muscle activity having a signal related to the subject's electrical muscle activity.

11. The portable therapy system in claim 8, wherein the processor is comprised in the remote communication station, the remote communication station being a cell phone or computer.

12. The portable therapy system in claim 11, wherein the stimulus is a video game.

13. The portable therapy system in claim 11, wherein the system weight is less than 15 lbs.

14. The portable therapy system in claim 10, wherein two-way communication system is further configured to provide an interface to enable a physician, clinician, or technician to access the signal related to the subject's arm or leg motion and the signal related to subject's body motion, and the preprogrammed or determined therapy parameters.

15. A portable therapy system for rehabilitation of a subject's movement disorder comprising:

a first sensor for measuring a subject's external body motion the first sensor having a signal related to the subject's external body motion;

a second sensor for measuring the subject's electrical muscle activity having a signal related to the subject's electrical muscle activity;

a device for providing a stimulus or instructions to the subject, the stimulus or instructions adapted to evoke a response from the subject in the form of external body motion and electrical muscle activity being measured;

a therapy device adapted to provide therapy to the subject according to preprogrammed therapy parameters or determined therapy parameters where the determined therapy parameters are based in part on external body motion of the subject measured in response to a prior stimulus or instructions; and a two-way communication system comprising a remote communication station, the remote communication station configured to be situated more than 200 feet away from the subject, the communication system adapted to:

1) Allow communication between components local to the subject, including at least the sensor and the device for providing a stimulus or instructions to the subject, and the remote communication station, 2) Transmit measured data to the remote communication station and receive data related to the measured data and/or to therapy parameters from the remote communication station, 3) Transmit therapy parameters to the subject's therapy device such that the therapy device provides therapy to the subject according to the adjusted therapy parameters, a processor programmed to:

1) Determine a task or activity the subject is performing based on measured electrical muscle activity and the stimulus or instructions provided to the subject, and 2) Calculate adjusted therapy parameters based at least in part on the subject's response to the stimulus or instructions and in part on the determined task or activity; and wherein the processor is further programmed to calculate the subject's ability to respond to the stimulus or instructions based in part on the signals of the first and second sensors.

16. The portable therapy system in claim 15, wherein the therapy device is a device worn by the subject to provide FES to at least one of the subject's muscles to supplement a response of the subject.

17. The portable therapy system in claim 15, wherein the processor is comprised in the remote communication station, the remote communication station being a cell phone or computer.

18. The portable therapy system in claim 17, wherein the stimulus is a video game.

19. The portable therapy system in claim 15, wherein the system weight is less than 15 lbs.

20. The portable therapy system in claim 15, wherein the two-way communication system is further configured to provide an interface to enable a physician, clinician, or technician to access the signal related to the subject's external body motion and the signal related to subject's electrical muscle activity, and the preprogrammed or determined therapy parameters.

\* \* \* \* \*